United States Patent [19]

Barrows et al.

[11] Patent Number: 4,719,917

[45] Date of Patent: Jan. 19, 1988

[54] SURGICAL STAPLE

[75] Inventors: Thomas H. Barrows, Cottage Grove; Harold E. Froehlich, St. Anthony, both of Minn.

[73] Assignee: Minnesota Mining and Manufacturing Company, St. Paul, Minn.

[21] Appl. No.: 14,867

[22] Filed: Feb. 17, 1987

[51] Int. Cl.⁴ .............................................. A61B 17/04
[52] U.S. Cl. ............................. 128/334 R; 128/334 C; 128/335.5; 128/337; 128/92 YR; 227/DIG. 1; 411/447; 411/457; 623/66
[58] Field of Search ............... 128/334 R, 334 C, 335, 128/335.5, 337, 346, 92 YC, 92 YE, 92 YF, 92 YR; 227/19, DIG. 1; 411/447, 460; 623/13, 66

[56] References Cited

U.S. PATENT DOCUMENTS

| | | | |
|---|---|---|---|
| 3,875,937 | 4/1975 | Schmitt et al. | 128/156 |
| 4,060,089 | 11/1977 | Noiles | 128/325 |
| 4,275,813 | 6/1981 | Noiles | 206/339 |
| 4,317,451 | 3/1982 | Cerwin et al. | 128/325 |
| 4,321,002 | 3/1982 | Froehlich | 411/457 |
| 4,345,601 | 8/1982 | Fukuda | 128/334 R |
| 4,428,376 | 1/1984 | Mericle | 128/335 |
| 4,434,796 | 3/1984 | Karapetian et al. | 128/92 YC |
| 4,513,746 | 4/1985 | Aranyl et al. | 128/334 |
| 4,532,926 | 8/1985 | O'Holla | 128/334 |
| 4,534,350 | 8/1985 | Golden et al. | 128/334 |
| 4,534,352 | 8/1985 | Korthoff | 128/334 |
| 4,585,458 | 4/1986 | Kurland | 623/13 |
| 4,637,380 | 1/1987 | Orejola | 128/334 C |

FOREIGN PATENT DOCUMENTS 0004554 of 1888 United Kingdom ........... 128/92 YF

Primary Examiner—Richard J. Apley
Assistant Examiner—Paul Prebilic
Attorney, Agent, or Firm—Donald M. Sell; James M. Smith; Lorraine R. Sherman

[57] ABSTRACT

A surgical staple and method for its use in closing an opening in mammalian tissue are disclosed. The staple comprises a central portion of strong, ductile, non-absorbable material and lower leg portions of absorbable material positioned at opposite ends of the central portion. The staple when closed is bent in the central portion to form a crown portion, so that the lower leg portions are in positions which approximate one another. After engagement, the lower leg portions extend through the tissue on either side of a closed opening so as to hold the tissue firmly in the closed position. After sufficient tissue healing has occurred, the biodegradable lower leg portions will loosen from the central portion, thus allowing for facile removal of the central portion.

16 Claims, 11 Drawing Figures

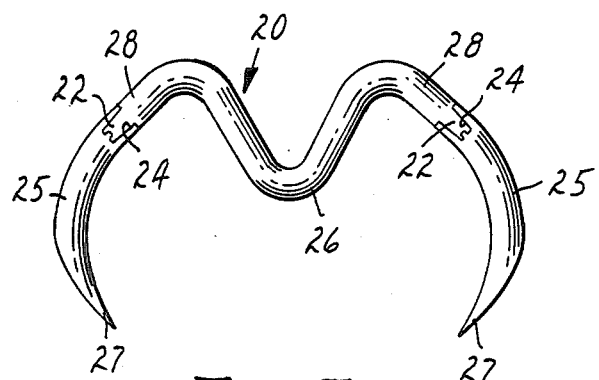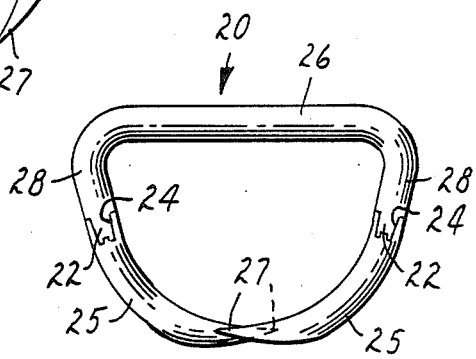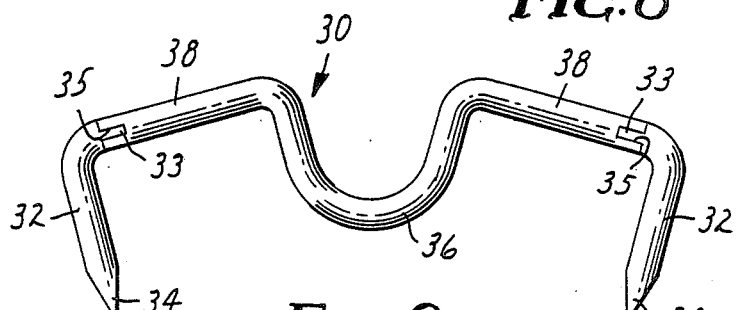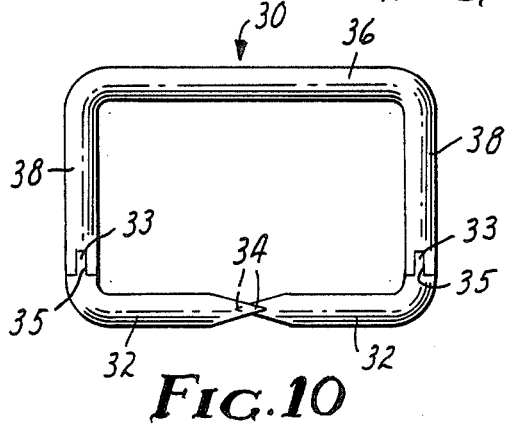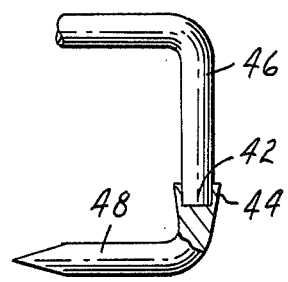

SURGICAL STAPLE

FIELD OF THE INVENTION

The present invention relates to a surgical skin staple comprising bioabsorbable and nonabsorbable parts. In another aspect, a method of stapling skin using the staple of the invention is disclosed.

BACKGROUND OF THE INVENTION

The use of surgical stapling as a method for suturing has increased dramatically in recent years. Staples have been used both internally and in the skin. The first staples used were metallic staples, and they are still widely used; see, for example, U.S. Pat. No. 4,321,002. For internal use metallic staples are frequently permanently implanted, while metallic staples in the skin are removed as soon as healing permits. For some purposes two piece staples are used wherein a fastening member and receiving member are used. Although these two piece staples were initially metallic, several polymeric fasteners have now been described, for example in U.S. Pat. Nos. 4,532,926; 4,534,352; and 4,534,350. A multipart surgical fastener for inserting multiple staples in soft body tissue (but not skin) includes "absorbable plastic" parts and is described in U.S. Pat. Nos. 4,060,089 and 4,513,746.

Polymeric surgical staples designed for use in one piece are limited, but a one piece device using a hinge and cam principle is described in U.S. Pat. No. 4,428,376. U.S. Pat. No. 4,317,451 discloses plastic surgical staples which can be made of totally absorbable or totally nonabsorbable materials.

The type of staple commonly used for stapling skin is different from most other staples. Skin staples, to be closed, are acted upon by forces only from one side of the stapled medium, whereas other types of staples are acted upon by forces above and below the stapled medium. Such skin staples may be supplied singly or in array for use in a cartridge or stapling instrument. An example of an array of metallic staples bonded together by a biodegradable absorbable plastic is found in U.S. Pat. No. 4,275,813.

SUMMARY OF THE INVENTION

Briefly, the present invention provides a novel staple for use in mammalian tissue comprising a conventional central portion of strong, ductile material physically or chemically coupled to bioabsorbable legs, the staple being used in a process for stapling tissue which does not require a special tool for removal.

The staple of the present invention has certain advantages compared with skin staples known in the art. It requires no significant modification of either insertion hardware or user procedures for insertion; the load-bearing strength and ductility of the preferably metallic central portion is maintained; staple removal is required only for the central portion; the pain of removal is minimized since the bioabsorbable legs remain embedded; and the cost of staple removal can be eliminated since it can be carried out by the patient rather than by medical personnel.

In this application:

"bioabsorbable" means that a substantial portion (preferably greater than 50%) is gradually degraded by mammalian tissue to the point that it is no longer present at the implant site and is metabolized by and/or excreted from the body;

"nonabsorbable" means resistant to degradation by hydrolysis and/or enzymatic attack in mammalian tissue;

"degraded" means broken down chemically so as to provide species with lower molecular weight and/or different chemical structure;

"coupled" means a joining by physical (e.g., mechanical) means, as by use of a socket, rivet, pin, crimp, screw, tongue and groove, locking taper, or chemical means, as by use of adhesive (cyanoacrylate, hot melt, pressure-sensitive, priming, and the like);

"mammalian tissue" means living tissue, mucous membranes, skin, gingival tissue, and the like of a mammal;

"lower leg portions" means the bioabsorbable portion of a staple that can be curved (e.g. arcuate), or bent, and having tapered and pointed ends;

"upper leg portions" means the parts of the central portion provided by subjecting the central portion to bending;

"central portion" means a wire-like or hollow metal member of a staple out of which a crown and upper leg portions are formed; it can be initially straight, curved, or combinations thereof;

"crown" means the portion of the staple external to the skin when the staple is implanted;

"closed shape" means that when the staple is bent into its fully implanted configuration, it has a circular, elliptical, rectangular, square, D-shape, or variation or modification thereof, with the tips essentially directly apposed (touching or not touching) or overlapping; and "approximating" means touching, not touching but aligned with a gap, or overlapping.

BRIEF DESCRIPTION OF THE DRAWING

FIG. 7, a fourth embodiment, shows a staple having a curved central portion which is generally "u", "v" or "m" shaped and having arcuate lower leg portions;

FIG. 8 shows the skin staple of FIG. 7 in closed position which forms a D-shaped configuration;

FIG. 9, a fifth embodiment, shows a staple having a curved central portion which is generally "u", "v", or "m" shaped and having bent lower leg portions;

FIG. 10 shows the staple of FIG. 9 in a closed position; and

FIG. 11 shows a portion of a staple of a sixth embodiment in which coupling is achieved by adherance.

DETAILED DESCRIPTION OF THE INVENTION

The present invention provides a surgical staple for use in closing an opening in mammalian tissue, the staple, when open, comprising a central portion of strong, ductile, non-absorbable material, and lower leg portions at opposite ends of the central portion, the lower leg portions comprising bioabsorbable material and flanking the central portion and having points at their ends and being joined by coupling means to the central portion, which staple when closed is bent in the central portion to form the crown portion and upper leg portions which with the bioabsorbable lower leg portions form generally into a closed shape with the lower leg portions in a position approximating one another so that each of the lower leg portions of the staple can extend through the tissue on one side of the closed tissue opening so as to hold the tissue firmly in closed position.

Figure 3:
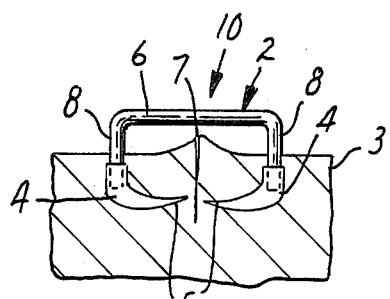
FIG. 3 shows the skin staple of FIG. 1 in a fully closed configuration.
Figure 4:
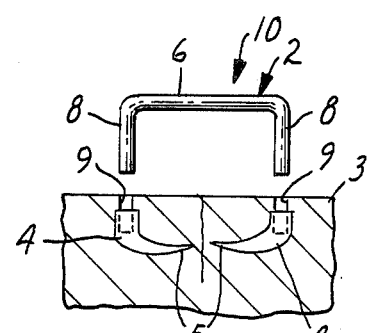
FIG. 4 shows the skin staple of FIG. 1 wherein the central portion is separated from implanted lower leg portions.
Figure 5:
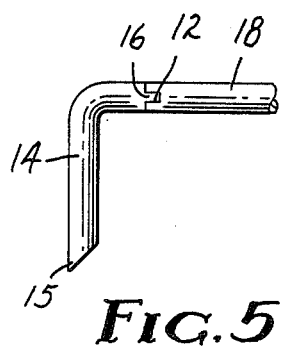
FIG. 5 shows a portion of a second embodiment of a staple of the invention having tongue and groove coupling means.
Figure 6:
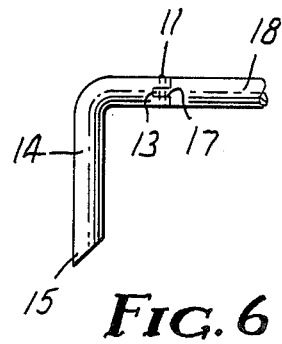
FIG. 6 shows a portion of a staple of a third embodiment having a tongue and groove coupling means which includes a pin for joining the central portion of the staple to the lower leg portion.

The mechanical coupling means between the central portion of the staple and the bioabsorbable lower leg can be a socket that frictionally or telescopically receives the lower leg, as illustrated in the Drawing in FIGS. 1, 2, 3, and 4, or it can be a tongue and groove frictional coupling means as in FIGS. 5, 6, 7, 8, 9 and 10, or combinations of any of these coupling means. For example, the central portion of the staple as shown in FIG. 5 can be a hollow tube or it can be a solid wire. In the embodiment of FIG. 6, the coupling means can be a mechanical fastener (i.e., tongue and groove) with, for example, a bioabsorbable pin or rivet. In still another embodiment as shown in FIG. 11, a bioabsorbable lower leg is caused to adhere to the metal central portion of the staple during an insert injection molding process.

The present invention also relates to a method of suturing wherein the upper portion of a two-component (one of the two components represents two parts which are the same, i.e. two legs) one-piece staple is removed from a stapled site after the bioabsorbable legs have been partially degraded.

The upper portion of the staple of the present invention maintains its integrity and is generally metallic, but could be any material which meets the needs of strength and ductility and is tissue-compatible. For example the upper portion is a nondegradable material which preferably is any conventional surgical metal, including alloys, which is suitable as a metallic staple component, e.g., stainless steel, such as 316L stainless steel, titanium, steel alloys, titanium alloys, nickel chromium alloy (Nichrome TM), nickel/cobalt/chrome, or combinations thereof.

The lower leg portion of the skin staple of the invention can be any bioabsorbable materials whether natural or synthetic. Synthetic bioabsorbable polymers are preferred. Copolymers or combinations of suitable bioabsorbable polymers are also included within the scope of suitable materials. That is, the lower staple legs of the invention can consist of a mixture or combination of two or more bioabsorbable polymers. Natural polymers are preferably used in admixture with synthetic polymers. Representative bioabsorbable natural and synthetic polymers include:

Natural Polymers (1) Partially oxidized cellulose surgical hemostats (see U.S. Pat. No. 3,364,200) such as Oxycel TM (fibrous surgical hemostatic material, Parke-Davis) and Surgicel TM (woven fabric hemostatic material, Surgikos).

(2) Chitin and/or chitin derivatives (e.g. U.S. Pat. No. 4,074,366).

(3) Collagen, regenerated collagen or catgut suture material.

Synthetic Polymers (1) Polyamino acids, polyamino acid copolymers and derivatives such as partially esterified poly-L-glutamic acid (U.S. Pat. No. 3,371,069), amino acid-hydroxy acid copolymer (U.S. Pat. No. 3,773,737), and nylon 2/nylon 6 copolymer (W. J. Bailey, et. al., "Biodegradable Polyamides", *Proceedings of 3rd International Biodegradation Symposium*, Sharpley and Kaplan eds., Applied Science Publishers Ltd., London, 1976, p. 765–773).

(2) Polyesters formed from diols and succinic and/or oxalic acid such as those described in U.S. Pat. Nos. 4,032,993 and 3,883,901, isomorphic copolyoxalates (U.S. Pat. No. 4,141,087), and poly(alkylene oxalates) (U.S. Pat. No. 4,140,678).

(3) Polymalic acid (U.S. Pat. No 4,265,247).

(4) Polydioxanone (U.S. Pat. No. 4,052,988).

(5) Poly-beta-hydroxy acids such as polyhydroxybutyrate (U.S. Pat. No. 3,225,766).

(6) Poly-alpha-hydroxy acids such as polyglycolic acid, polylactic acid, (U.S. Pat. No. 3,636,956), copolymers of lactic and glycolic acids, (U.S. Pat. No. 4,137,921), and said polymers copolymerized with other polyesters (U.S. Pat. No. 4,118,470).

(7) Polymers made from unsymmetrically-substituted 1,4-dioxane-2,5-diones (U.S. Pat. No. 3,960,152).

(8) Polyesteramides such as those described in U.S. Pat. Nos. 4,209,607 and 4,343,931.

(9) Copolymers of glycolide and trimethylene carbonate such as described in U.S. Pat. No. 4,429,080.

(10) Polycaprolactone and copolymers of lactide with epsilon caprolactone such as described in U.S. Pat. No. 4,057,537.

Preferred biodegradable polymers and copolymers for use in the invention are polylactic acid (U.S. Pat. No. 3,636,956), polyglycolic acid (U.S. Pat. No. 3,297,033), polydioxanone (U.S. Pat. No. 4,052,988), copolymers of glycolide and trimethylene carbonate (U.S. Pat. No. 4,429,080), poly(lactide-co-glycolide) (U.S. Pat. No. 4,137,921) and poly(esteramides) such as poly(oxysuccinoyloxydodecane-1,12-di(amidocarbonylmethylene)-co-10 percent-oxysuccinoyloxy-4,9-dioxadodecane-1,12-di(amidocarbonylmethylene)] and poly[oxysuccinoyloxyhexane-1,6-di(amidocarbonylmethylene)] (U.S. Pat. No. 4,343,931), and mixtures thereof. These polymers and copolymers are preferred because they are known to be well tolerated by the body upon implantation in addition to being bioabsorbable. Mixtures of polymers allow for variation of properties of the staple legs.

The bioabsorbable lower legs of the skin staple of the invention are selected to provide sharp, penetrating tips which release from the central portion of the staple at a specific time post-implantation thereby permitting painless removal or sloughing of the staple crown and upper legs. The release time can be varied, for example, by choice of bioabsorbable lower leg material, the coupling means and its configuration, and the configuration between the interface of metal and polymer.

The bioabsorbable polymer lower legs (which include tips) can readily be insert injection molded onto the ends of the upper leg portions of the central portion of the staple. The bond between the lower and upper leg portions can be an adhesive one that results from the cooling of the polymer in contact with metal. Part of the adhesion results from shrinkage of the polymer upon cooling when it is in a configuration so as to surround the metal upper leg portion as is shown in FIG. 11. Other conventional methods such as casting from a solvent or melt pressing can also be used. Alternatively, polymer tips can be inserted into hollow metal tubes at the ends of the upper leg portions. In such a case, a bioabsorbable adhesive can be useful. In such metal tubes various mechanical or friction means for locking in the polymer lower legs can be used, see, for example, FIGS. 5 and 6. Other locking mechanisms include a locking taper, a screw, a rivet, etc. Lower leg portions can be reinforced using polymer in combination with inorganic compounds such as tricalcium phosphate, potassium meta-phosphate, or hydroxylapatite, or resorbable glasses and ceramics such as those described by *Orthopedics*, 8:7, 907–915 (July 1985).

Figure 1:
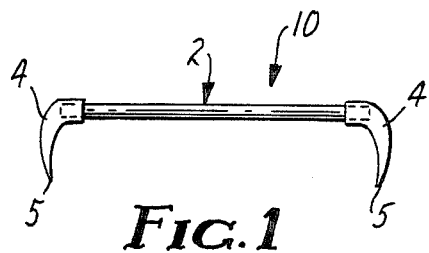
FIG. 1 shows an elevational view of one embodiment of a skin staple of the present invention in open configuration.

Referring now to the Drawing, FIG. 1 shows one embodiment of a staple 10 of the invention in open position. Central wire portion 2 is frictionally attached to bioabsorbable lower legs 4 having tips 5.

Figure 2:
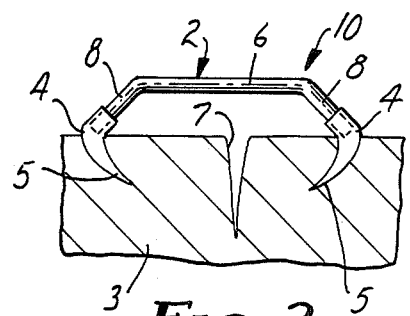
FIG. 2 shows the skin staple of FIG. 1 in a partially closed configuration.

In FIGS. 2, 3, and 4 various configurations of a surgical staple of the invention are shown. Staple 10 is shown in FIG. 2 (partially closed) and in FIG. 3 (closed position). The crown 6 and upper leg portions 8 are metallic of solid or hollow stock and the lower legs 4 are made of a bioabsorbable material. The staple can be dispensed from a conventional mechanical device and can be inserted by means of sharp, needle-like tips 5 into the skin 3 to close a break 7 in the skin 3 such as a wound as shown in FIGS. 2 and 3. FIG. 4 shows the wound 3 to 7 days post implantation where sufficient healing has taken place to permit staple removal. The crown 6 and upper leg portions 8 of staple 10 have been separated from the bioabsorbable lower leg portions 4 and explanted from the tissue by application of gentle traction on the exposed crown 6. This can be accomplished, for example, by the patient plucking out the metal using fingernails, or by the action of a wash cloth used during bathing. An alternative method for rapid staple removal is to place a strip of adhesive tape on top of a row of staples in the skin and then to quickly strip off the tape which will pull out all the staple crowns.

The absorbable lower legs 4 and tips 5, which are not necessarily completely absorbed at this time, remain buried under the skin and are slowly absorbed by the body. Times for absorption can range from about 2 months to about 2 years depending on the composition of the lower leg portions and their shapes. Polymer thus implanted should have no effect on the rapid healing of the holes 9 (shown in FIG. 4) made by the staple 10 once the crown 6 is removed.

Various curved and angled staples and staple tips using various arcuate aspect ratios can be used and are contemplated as part of the invention.

FIGS. 5 and 6 show enlarged fragmentary portions of a staple of the invention. Upper leg portion 18 is mechanically coupled, by a means having tongue 16 and groove 12, to bioabsorbable lower leg portion 14 having tip 15. In FIG. 6, it can be seen that pin 11, which is bioabsorbable, secures the tongue 13 and groove 17 coupling means.

FIG. 7 shows staple 20 in open position having curved crown 26, upper leg portions 28, and arcuate lower leg portions 25 with sharp tips 27. The coupling means has tongue 22 and groove 24. FIG. 8 shows staple 20 in closed position so as to form a D-shaped configuration with tips 27 closely approximating (in this case, slightly overlapping) each other.

FIG. 9 shows staple 30 in open position having curved crown 36, upper leg portions 38, and bent lower legs 32 with sharp tips 34. The coupling means has tongue 33 and groove 35. FIG. 10 shows staple 30 in closed position so as to form a rectangular-shaped configuration with lower leg tips 34 in close approximation and slightly overlapping.

FIG. 11 shows an enlarged fragmentary portion of a staple, another embodiment, of the invention. Upper leg portion 46 is adhesively coupled to lower leg portion 48 as a result of an injection molding process in which end part 42 of upper leg portion 46 is pressed into end part 44 of lower leg portion 48 when lower leg portion 48 is in a molten state. It is also within the scope of the present invention to utilize a bioabsorbable adhesive to adhere upper leg portion 46 and lower leg portion 48 together.

In addition to the characteristics of materials being employed, other factors influence a satisfactory and cosmetically appealing skin closure. Skin thickness varies from patient to patient and also with the particular body surface being stapled. This in turn, necessitates the use of differing implantation techniques and in some cases a staple of different design. Skin thickness, application technique, and staple design all impact staple performance. Staples have been known to fall out of the skin, fail to puncture the skin, let the wound gap open, gather excessive amounts of tissue, invert the skin edges, produce a stepped closure at the incision line, rotate in the wound, and fail to close properly.

A satisfactory staple design must eliminate, or at least minimize these performance deficiencies. Aside from the material properties, there are certain geometric design parameters which alter staple performance. From an analytical standpoint, eleven staple performance characteristics have been defined and are measureable. These are: linear gather, compression ratio, staple rotation, gathering angle, penetration angle, tissue scarring, penetration force, removal characteristics, staple formation forces, actuator staple interactions, and anvil restraint requirements.

In analysing staple performance, the single most important aspect is the path various points on the staple tip follow as the staple is closed. Particular designs perform better in certain situations. FIG. 1 shows an example of a staple which gathers a lot of tissue. FIG. 7 shows example of a staple that punctures a wide range of skin thicknesses very well. FIG. 9 shows an example of a staple which maintains an everted skin edge.

Objects and advantages of this invention are further illustrated by the following examples, but the particular materials and amounts thereof recited in these examples, as well as other conditions and details, should not be construed to unduly limit this invention.

EXAMPLE 1

In order to demonstrate that an absorbable polymer component will in fact separate from a wire component at a useful time post-implantation, an in vitro evaluation using pH 7.4 Krebs-Ringer phosphate solution at 37° C. to simulate physiological conditions was performed. The samples were made from melt pressed films of poly[N,N'-dodecamethylenebis(amidomethylene)succinate-co-10%-N,N'-4,9-dioxadodecamethylenebis-(amidomethylene)succinate] prepared according to the procedure of Example 11 in U.S. Pat. No. 4,529,792 and Nichrome TM wire (24 guage). Films of two different thicknesses (29 samples of 0.28 mm thickness and 27 samples of 0.38 mm) were each cut into pieces measuring 5×10 mm. Wire was cut into 10 cm lengths and a loop was formed at one end of each piece. The straight end was then heated in a flame and carefully pressed into the center of a polymer sample resting on a block of polytetrafluoroethylene (Teflon TM, Dupont) to provide a coupling means similar to that of FIG. 1.

The polymer-wire samples were placed in the Krebs-Ringer solution at 37° C. and tested periodically by supporting the polymer and hanging a 150 g weight on the wire loop. Under these conditions the wire either pulled out of the polymer and was noted as a release or remained embedded and was returned to the 37° C. solution for further soaking.

The 150 g dead load release limit was selected after determining that twice this value is approximately the maximum weight that can be supported on the volar surface of the index fingernail without causing discomfort.

As shown in TABLE I, the average time required for release of the wire from the polymer in vitro was 1.1 days for a 0.28 mm deep embedding and 1.8 days for a 0.38 mm deep embedding. These values demonstrate that the polymer in this Example was useful for the present staple application.

EXAMPLE 2

Poly(L-lactide-co-30%-glycolide) was synthesized according to a publised procedure (D. K. Gilding and A. M. Reed, Biodegradable Polymers for Use in Surgery-Polyglycolic/Polylactic acid) Homo- and Copolymers, *Polymer*, 20, 1459–1464, 1979). The polymer was melt pressed into 0.33 mm and 0.56 mm thick sheets and cut into 5×10 mm test samples. Nichrome wires were embedded in the samples and tested as described in Example 1. As shown in TABLE I, release of wire from the poly(lactide-glycolide) sample was dependent on the thickness of the film (i.e. depth of wire embedding). The 0.33 mm thick polymer released from the wire after an average of 1.5 days, whereas the 0.56 mm sample released after an average of 3.2 days. Since staple removal is normally permissible after 3 to 7 days, these data indicate that an ideal value for release performance can be achieved with this type of polymer.

EXAMPLE 3

A 0.33 mm thick sheet of polydioxanone was obtained by melt pressing commercially available size 2-0 polydioxanone (PDS TM) violet monofilament absorbable sutures (Ethicon, Inc., Somerville, NJ 08876). Polydioxanone reprocessed in this manner gave a soft, somewhat rubbery material. In the actual manufacture of staples, the molten polydioxanone could be solidified under controlled conditions which develop higher crystallinity and thus greater stiffness. Samples of wire embedded in polydioxanone and tested as described in the previous examples released after an average of 1.2 days in vitro (TABLE I). The data show that the polydioxanone-metal bond is also susceptible to moisture induced loosening and can be utilized in the manufacture of staples of the present invention.

TABLE I

Release of 24 guage Nichrome wire from synthetic absorbable polymers under a 150 g load in pH 7.4 Krebs-Ringer phosphate solution at 37° C.

| Polymer | Thickness (mm) | Number of samples | Day no.: 0 | 1 | 2 | 3 | 4 | 5 | 6 | 7 | 8 | Average time to release (days) |
|---|---|---|---|---|---|---|---|---|---|---|---|---|
| poly(esteramide) | 0.28 | 29 | 0 | 27 | 2 | — | — | — | — | — | — | 1.1 |
| poly(esteramide) | 0.38 | 27 | 0 | 8 | 17 | 1 | 1 | — | — | — | — | 1.8 |
| poly(lactide-glycolide) | 0.33 | 32 | 0 | 20 | 8 | 3 | 1 | — | — | — | — | 1.5 |
| poly(lactide-glycolide) | 0.56 | 32 | 0 | 6 | 10 | 6 | 3 | 1 | 2 | 2 | 2 | 3.2 |
| polydioxanone | 0.33 | 26 | 0 | 22 | 4 | — | — | — | — | — | — | 1.2 |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A surgical staple for use in closing an opening in mammalian tissue, said staple, when open, comprising a central portion of strong, ductile, non-absorbable material, and lower leg portions at opposite ends of the central portion, said lower leg portions comprising bioabsorbable material and flanking said central portion, said lower leg portions having points at their ends and being joined by coupling means to said central portion, such staple when closed is bent in the central portion to form a crown portion and upper leg portions which with said lower leg portions form generally into a closed shape with said lower leg portions in a position approximating one another so that each of said lower leg portions of the staple can extend through the tissue on one side of the closed opening so as to hold said tissue firmly in closed position.

2. The staple according to claim 1 wherein said coupling means is a socket that frictionally receives said lower leg portions of said staple.

3. The staple according to claim 1 wherein said coupling means is a tongue and groove frictional coupling means.

4. The staple according to claim 1 wherein said coupling means is a mechanical fastener.

5. The staple according to claim 1 wherein said coupling means is an adhesive bond.

6. The staple according to claim 5 wherein said adhesive bond is formed by insert injection molding.

7. The staple according to claim 4 wherein said mechanical fastener comprises a rivet or pin.

8. The staple according to claim 1 wherein said bioabsorbable material is a natural or synthetic polymer or a combination thereof.

9. The staple according to claim 8 wherein said bioabsorbable material is a synthetic polymer selected from the group consisting of polyglycolic acid, polylactic acid, polycaprolactone, poly(esteramides), polydioxanone, and copolymers and mixtures thereof.

10. The staple according to claim 8 wherein said bioabsorbable material is a poly(esteramide).

11. The staple according to claim 1 wherein said central portion comprises at least one surgical metal or alloy.

12. A method of surgically stapling mammalian tissue comprising the steps of:
(a) implanting at least one staple which when open comprises a central portion of strong, ductile, nonabsorbable material, and lower leg portions at opposite ends of the central portion, said lower leg portions comprising bioabsorbable material and flanking said central potion, said lower leg portions having points at their ends and being joined by coupling means to said central portion, which staple when closed is bent in the central portion to form a crown portion and upper leg portions which with said lower leg portions form generally into a closed shape with said lower leg portions in a position approximating one another so that each of said lower leg portions of the staple can extend through the tissue on one side of the closed opening so as to hold said tissue firmly in closed position, and
(b) removing said central portion of said staple when sufficient tissue healing has occurred and said bioabsorbable lower legs have loosened sufficiently to allow removal of said central portion.

13. The method according to claim 12 wherein said bioabsorbable polymer of said lower leg portion of said staple is a synthetic or natural polymer or a combination thereof.

14. The method according to claim 12 wherein said bioabsorbable material of said lower leg portions of said staple is a synthetic polymer selected from the group consisting of polyglycolic acid, polylactic acid, polycaprolactone, poly(esteramides), polydioxanone, and copolymers and mixtures thereof.

15. The method according to claim 14 wherein said bioabsorbable material is a poly(esteramide).

16. The method according to claim 12 wherein said central portion of said staple comprises at lesat one surgical metal or alloy.

* * * * *